United States Patent [19]

McGuckin et al.

[11] Patent Number: 5,811,225

[45] Date of Patent: Sep. 22, 1998

[54] PHOTOGRAPHIC REVERSAL SOLUTION AND METHOD OF USE

[75] Inventors: Hugh G. McGuckin, Rochester; John S. Badger, Webster; Edgardo Lopez, Hilton; Paul A. Schwartz, Webster, all of N.Y.

[73] Assignee: Eastman Kodak Company, Rochester, N.Y.

[21] Appl. No.: 815,771

[22] Filed: Mar. 12, 1997

[51] Int. Cl.⁶ .................................................. G03C 7/407
[52] U.S. Cl. ........................................... 430/407; 430/379
[58] Field of Search ..................... 430/379, 407

[56] References Cited

U.S. PATENT DOCUMENTS

| | | | |
|---|---|---|---|
| 3,617,282 | 11/1971 | Bard et al. | 430/379 |
| 4,623,612 | 11/1986 | Nishikawa et al. | 430/379 |
| 4,921,779 | 5/1990 | Cullinan et al. | 430/379 |
| 4,975,356 | 12/1990 | Cullinan et al. | 430/393 |
| 5,037,725 | 8/1991 | Cullinan et al. | 430/372 |
| 5,523,195 | 6/1996 | Darmon et al. | 430/393 |
| 5,552,264 | 9/1996 | Cullinan et al. | 430/372 |

OTHER PUBLICATIONS

Benzalkonium chloride, Condensed Chemical Dictionary, 8th Ed., 1971.

*Primary Examiner*—Hoa Van Le
*Attorney, Agent, or Firm*—J. Lanny Tucker

[57] ABSTRACT

Color reversal photographic films are processed using a reversal solution comprising stannous ion and a quaternary ammonium compound as the sole biocide, to reduce formation of biogrowth.

17 Claims, No Drawings

PHOTOGRAPHIC REVERSAL SOLUTION AND METHOD OF USE

RELATED APPLICATION

Copending and commonly assigned U.S. Ser. No. 08/820,323, filed on even date herewith by Buongiorne and Haight, and entitled "Photographic Reversal Bath Concentrate and Method of Preparing Same".

FIELD OF THE INVENTION

This invention relates in general to color photography and in particular, to a photographic reversal solution and a method of processing color reversal photographic films. More particularly, the invention relates to an improved reversal solution that has improved antimicrobial agents, and thus forms less sludge in processing tanks, and to a method for its use.

BACKGROUND OF THE INVENTION

Multicolor, multilayer photographic elements are well known in the art. Such materials generally have three different selectively sensitized silver halide emulsion layers coated on one side of a single support. Each layer has components useful for forming a particular color in an image. Typically, the materials utilize color forming couplers or dyes in the sensitized layers during processing.

One commercially important process intended for use with color reversal photographic films useful for providing positive color images, can include the following sequence of steps: first (or black-and-white) development, washing, reversal reexposure, color development, bleaching, fixing, and washing and/or stabilizing. Another useful process is similar but includes stabilizing between color development and bleaching. Such conventional steps are described, for example, in U.S. Pat. No. 4,921,779 (Cullinan et al), U.S. Pat. No. 4,975,356 (Cullinan et al), U.S. Pat. No. 5,037,725 (Cullinan et al), U.S. Pat. No. 5,523,195 (Darmon et al) and U.S. Pat. No. 5,552,264 (Cullinan et al).

Thus, it is known that after the first development, the exposed films are subjected to a reversal reexposure and subsequent color development. Certain nucleating agents have been used in a solution applied after the first development in place of reversal reexposure. Such a solution is known as a "reversal bath". Very early reversal baths contained certain boron compounds as nucleating agents, but they had a number of disadvantages that led to improvements with the use of stannous salts that are stable in both acidic and alkaline environments.

The nucleating agents in the reversal bath are intended to reduce silver ion remaining undeveloped from the first development step. Commercial reversal baths generally contain stannous ion as the silver ion reducing agent, as described for example, in U.S. Pat. No. 3,617,282 (Bard et al). Stannous ion is generally provided in the form of a simple or chelated salt.

Commercial reversal bath solutions, however, can exhibit a number of problems. They may give off an unpleasant odor due to the presence of volatile organic acids typically used as buffers, and undesirable biogrowth may occur in the processing tank. In addition, reversal bath solutions may require filtration after certain hours of use because of the build-up of predominately organic precipitates from high biological matter. Reduction of such biogrowth is a considerable challenge in the art. This would reduce the need for filtration, filter changes and other costly maintenance.

The microbial population in most commercial "seasoned" or used reversal bath solutions is commonly on the order of at least $10^5$ CFU/ml (colony forming units/ml). This causes customer dissatisfaction because of the need for more frequent bath replacement and processor tank cleaning. Thus, there is a need to reduce this level of bacterial and fungal organisms in such solutions.

In addition, it would be desirable to have a reversal bath solution that is not susceptible to the other problems noted above (for example, sludge formation), and which continues to have the desirable photochemical properties obtained from the use of stannous ion.

SUMMARY OF THE INVENTION

The problems noted above have been solved with use of a photographic reversal solution comprising stannous ion and a quaternary ammonium compound as the sole biocide, the quaternary ammonium compound having a molecular weight of from about 175 to about 440.

This invention also provides a method of processing a color reversal photographic film comprising:

A) contacting an imagewise exposed, black-and-white developed color reversal photographic film with the reversal solution noted above, and B) color developing the film.

The reversal solution of this invention exhibits reduced odor and biogrowth (both fungal and bacterial) after lengthy use in the reversal bath tank, and this advantage is achieved by including in the solution a specific quaternary ammonium compound as the only biocide. Generally, this material is soluble in solution and does not form complexes with salts in the solution. It is highly compatible with the other essential components of the reversal bath solution, particularly in concentrated form. Thus, biogrowth is reduced without sacrificing photographic quality in the processed film.

In addition, the solution contains less odor-causing components, such as propionic acid, that are commonly used in commercial reversal solutions.

The reversal bath solution can be advantageously prepared from a concentrate such as that described in commonly assigned and copending U.S. Ser. No. 08/820,323, filed on even date herewith by Buongiorne and Haight, identified above.

DETAILED DESCRIPTION OF THE INVENTION

A wide variety of color reversal photographic elements can be used in the practice of the present invention. A detailed description of such materials is found, for example, in *Research Disclosure,* publication 36544, pages 501–541 (September 1994). *Research Disclosure* is a publication of Kenneth Mason Publications Ltd., Dudley House, 12 North Street, Emsworth, Hampshire PO10 7DQ England (also available from Emsworth Design Inc., 121 West 19th Street, New York, N.Y. 10011). This reference will be referred to hereinafter as *"Research Disclosure"*. More details about such elements are provided herein below.

Color reversal photographic elements utilized in the practice of this invention are comprised of a support having on one side thereof a plurality of photosensitive silver halide emulsion layers. The photosensitive layers can contain any of the conventional silver halides as the photosensitive material, for example, silver chloride, silver bromide, silver bromoiodide, silver chlorobromide, silver chloroiodide, silver chlorobromoiodide, and mixtures thereof. Useful support materials include cellulose acetate film, polyvinylacetal film, polycarbonate film, polystyrene film, polyethylene terephthalate film, and the like. The silver halide is dispersed within a suitable hydrophilic colloid such as gelatin or derivatives thereof. The silver halide emulsion layers can contain a variety of well-known addenda, including but not limited to, chemical sensitizers, development modifiers and antifoggants.

As explained above, color reversal processes of the prior art utilize a first developer, a reversal bath, a color developer, a conditioning solution, a bleach bath, a fixing bath and a stabilizer bath. The components that are useful in each of such baths are well known in the photographic art. The improved process of this invention can utilize the same baths except that the improved reversal solution of this invention is used instead of the conventional reversal bath solutions.

The first developer generally contains a black-and-white developing agent or a mixture thereof. Useful developing agents include, but are not limited to, dihydroxybenzene developing agents (such as hydroquinone), 3-pyrazolidone developing agents (such as 1-phenyl-3-pyrazolidone), and aminophenol developing agents (such as p-aminophenol). In addition to the developing agent, the first developer typically contains other agents such as preservatives, sequestering agents, restrainers, antifoggants, buffers and silver halide solvents.

The reversal solution of this invention is used following the first development step. A critical component is a nucleating agent such as stannous ions that are generally provided in the form of stannous salts or chelated stannous salts, as described for example in U.S. Pat. No. 3,617,282 (noted above), incorporated herein by reference. Particularly useful stannous salts include, but are not limited to, stannous chloride, stannous bromide, stannous fluoride and stannous acetate. Stannous chloride is preferred.

Stannous ions are generally present in the solution in an amount sufficient to provide the reversal exposure needed after the first development. The concentration can be at least 0.002 mol/l, and generally does not exceed about 0.02 mol/l. Preferably, the stannous ion concentration is from about 0.004 to about 0.01 mol/l.

Sources of stannous ions can be readily purchased from a number of commercial sources.

A second critical component of the reversal solution of this invention is a quaternary ammonium compound which is used as the sole biocide. Such materials have one or more quaternary nitrogen atoms in the molecule, and generally have a molecular weight of at least about 175 and less than about 440. Preferably, the molecular weight is from about 250 to about 420, and more preferably it is from about 300 to about 380.

Each quaternary nitrogen atom in the molecule has its four valences filled with nonpolymeric aliphatic, heterocyclic or carbocyclic groups.

As used herein, "aliphatic" refers to a monovalent organic radical having 1 to 30 carbon atoms in the backbone that can be interrupted with one or more oxy, thio, imino or carbonyl groups. Hydrogen atoms along the backbone can be replaced with fluorine atoms to provide fluorinated aliphatic groups. The aliphatic groups can be substituted with one or more halo atoms, aryl, alkoxy, amino, cycloalkyl or other groups as would be readily apparent to one skilled in the art.

As used herein, the term "heterocyclic" refers to a monovalent organic radical having at least one heterocyclic moiety in the backbone containing one or more oxygen, nitrogen or sulfur atoms. In addition, the heterocyclic group can include a quaternary ammonium group. The heterocyclic group can be aromatic or nonaromatic and generally includes up to 15 atoms in the mono- or polycyclic ring or nucleus which can be substituted with one or more other organic groups if desired as would be readily apparent to one skilled in the art.

The term "carbocyclic" refers to an organic monovalent radical that has all carbon atoms in a mono or polycyclic ring or nucleus, including cycloalkyl, cycloalkenyl and aryl groups. Such rings generally have up to 14 carbon atoms in the ring structure which can be substituted with one or more other organic groups as would be readily apparent to one skilled in the art.

Useful quaternary ammonium compounds that are biocides for this invention can also be represented by the formula III:

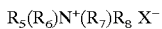

wherein $R_5$, $R_6$, $R_7$ and $R_8$ are independently nonpolymeric aliphatic, heterocyclic or carbocyclic radicals as defined above. $X^-$ is defined below. Preferably, each of the radicals is a monovalent heterocyclic or alkyl group, and the sum of the carbon and hetero atoms in the chains of all four groups is at least 10 and generally less than 20. Most preferably, at least one of the radicals has a chain length of at least 8 carbons, and up to 18 carbons, which can be interrupted with one or more nitrogen or oxygen atoms.

Alternatively, any two or three of the radicals of the noted structure can form a quaternary ring with the nitrogen atom, such as a pyridinium, piperidinium, pyrazinium, quinolinium or morpholino ring.

Particularly useful compounds in the reversal solution of this invention are those having quaternary nitrogens having its four valences filled with the same or different hydrocarbon groups having 1 to 20 carbon atoms as long as these are at least 10 carbon atoms for at least one group. Preferably, one or two of the hydrocarbon groups have 1 to 3 carbon atoms, and the remaining hydrocarbon groups are considerably larger, for example having at least 8 carbon atoms. More preferably, one of the groups has at least 12 carbon atoms, and each of the remaining groups has only 1 or 2 carbon atoms.

The anions ($X^-$) for the cationic compounds can be any suitable negatively charged monovalent ion such as a halide or anions of small organic or inorganic salts, such as acetates, that does not form a precipitate in solution or otherwise deleteriously affects the action of the reversal solution. Halides, such as chloride and bromide, are preferred.

Representative compounds useful in this invention include, but are not limited to, nonyltrimethyl ammonium bromide, dodecyltrimethyl ammonium chloride, hexadecyltrimethyl ammonium bromide (or cetyltrimethyl ammonium bromide), hexadecyltrimethyl ammonium chloride (or cetyltrimethyl ammonium chloride), benzyltriethyl ammonium chloride, didodecyldimethyl ammonium bromide, benzyldimethylphenyl ammonium chloride, tetrahexyl ammonium chloride, stearyldimethylbenzyl ammonium chloride, cetylpyridinium chloride, benzalkonium chloride (a mixture of alkyldimethylbenzyl ammonium chlorides), a mixture of alkyltrimethyl ammonium bromides (also known as "Cetrimide"), and myristyltrimethyl ammonium bromide. A most preferred compound is myristyltrimethyl ammonium bromide. Mixtures of such compounds can be used if desired since many of them are commercially available as mixtures.

Many of these compounds are available from a number of commercial sources, including Lonza Chemicals or Zeeland Chemicals Inc.. They may be supplied as pure compounds, aqueous solutions or as aqueous mixtures.

One compound not useful in the present invention is known as Hyamine 1622, benzethonium chloride, or (benzyldimethyl-2-{2-[4-(1,1,3,3-tetramethylbutyl) phenoxy]ethoxy}ethylammonium chloride. Its molecular weight is too high (about 448) and has been observed to result in cloudy solutions and precipitates in concentrated reversal solutions.

The quaternary ammonium compound useful in the practice of this invention is generally present in a concentration of at least about 50 ppm, with from about 50 to about 300 ppm being preferred, and from about 50 to about 250 ppm being more preferred. The particular amount of a given compound used in the reversal bath solution will depend upon its solubility and other factors. If the compounds have high solubility, the concentration may be higher, and the concentration may be even higher if the solution is formulated, stored or used in a concentrated form, as described in copending U.S. Ser. No. 08/820,323, of Buongiorne et al, noted above.

The reversal solution can also include other conventional components such as buffers and sequestering agents, or mixtures thereof. Useful sequestering agents include various known aminocarboxylic acids or aminopolyphosphonic acids or salts thereof. It is particularly advantageous that the solution does not contain propionic acid or other odor-producing carboxylic acids.

It may be desirable for the reversal solution to include one or more stannous ion stabilizers as are known in the art. Useful stabilizers include, but are not limited to, p-aminophenol, phenylenediamine and Bandrowski's base. Such stabilizers are present in conventional amounts, that is generally at least about 0.1 mg/l and preferably from about 0.2 to about 0.8 mg/l. p-Aminophenol is preferred.

It is particularly useful for the reversal solution to contain one or more organic phosphonic or phosphinic acid chelating agents. Such chelating agents can be generally represented by the structure I or II:

   (I)

or

   (II)

wherein n is 2 or 3, and preferably 3.

$R_1$ is hydrogen, a substituted or unsubstituted alkyl group of 1 to 12 carbon atoms (such as methyl, hydroxymethyl, ethyl, isopropyl, t-butyl, hexyl, octyl, nonyl, decyl, benzyl, 4-methoxybenzyl, β-phenethyl, o-octamidobenzyl or β-phenethyl), a substituted or unsubstituted alkylaminoalkyl group (wherein the alkyl portion of the group is an defined above, such as methylaminomethyl or ethylaminoethyl), a substituted or unsubstituted alkoxyalkyl group of 1 to 12 carbon atoms (such as methoxymethyl, methoxyethyl, propoxyethyl, benzyloxy, methoxymethylenemethoxymethyl, or t-butoxy), a substituted or unsubstituted cycloalkyl group of 5 to 10 carbon atoms (such as cyclopentyl, cyclohexyl, cyclooctyl or 4-methylcyclohexyl), a substituted or unsubstituted aryl group of 6 to 10 carbon atoms (such as phenyl, xylyl, tolyl, naphthyl, p-methoxyphenyl or 4-hydroxyphenyl), or a substituted or unsubstituted 5- to 10-membered heterocyclic group having one or more nitrogen, oxygen or sulfur atoms in the ring besides carbon atoms [such as pyridyl, pyrimidyl, pyrrolyldimethyl, pyrrolyldibutyl, benzothiazolylmethyl, tetrahydroquinolylmethyl, 2-pyridinylmethyl, 4-(N-pyrrolidino)butyl or 2-(N-morpholino)ethyl].

$R_2$ is hydrogen, a substituted or unsubstituted alkyl group of 1 to 12 carbon atoms (as defined above), a substituted or unsubstituted aryl group of 6 to 10 carbon atoms (as defined above), a substituted or unsubstituted cycloalkyl group of 5 to 10 carbon atoms (as defined above), a substituted or unsubstituted 5- to 10-membered heterocyclic group (as defined above), $-PO_nM_2$ or $-CHR_4PO_nM_2$.

$R_3$ and $R_4$ are independently hydrogen, hydroxyl, a substituted or unsubstituted alkyl group of 1 to 12 carbon atoms (as defined above) or $-PO_nM_2$.

M is hydrogen or a water-soluble monovalent cation imparting water-solubility such as an alkali metal ion (for example sodium or potassium), or ammonium, pyridinium, triethanolammonium, triethylammonium ion or others readily apparent to one skilled in the art. The two cations in each molecule do not have to be the same. Preferably, M is hydrogen, sodium or potassium.

In defining the substituted monovalent groups herein, useful substituents include, but are not limited to, an alkyl group, hydroxy, sulfo, carbonamido, sulfonamido, sulfamoyl, sulfonato, thioalkyl, alkylcarbonamido, alkylcarbamoyl, alkylsulfonamido, alkylsulfamoyl, carboxyl, amino, halo (such as chloro or bromo) sulfono, or sulfoxo, alkoxy of 1 to 5 carbon atoms (linear or branched), $-PO_nM_2$, $-CH_2PO_nM_2$ or $-N(CH_2PO_nM_2)_2$ wherein the alkyl (linear or branched) for any of these groups has 1 to 5 carbon atoms.

Representative phosphonic acids useful in the practice of this invention include, but are not limited to the compounds listed in EP 0 428 101A1 (page 4). Representative useful compounds are 1-hydroxyethylidene-1,1-diphosphonic acid, diethylenetriaminepentaphosphonic acid, ethylenediamine-N,N,N',N'-tetramethylenephosphonic acid, nitrilo-N,N,N-trimethylenephosphonic acid [also known as aminotris (methylenephosphonic acid)], 1,2-cyclohexanediamine-N, N,N',N'-tetramethylenephosphonic acid, o-carboxyaniline-N,N-dimethylenephosphonic acid, propylamine-N,N-dimethylenephosphonic acid, 4-(N-pyrrolidino)butylamine-N,N-bis(methylenephosphonic acid), 1,3-diamino-2-propanol-N,N,N',N'-tetramethylenephosphonic acid, 1,3-propanediamine-N,N,N',N'-tetramethylenephosphonic acid, 1,6-hexanediamine-N,N,N',N'-tetramethylenephosphonic acid, o-acetamidobenzylamine-N,N-dimethylenephosphonic acid, o-toluidine-N,N-dimethylenephosphonic acid, 2-pyridinylmethylamine-N,N-dimethylenephosphonic acid, 1-hydroxyethane-1,1-diphosphonic acid, diethylenetriamine-N,N,N',N'',N''-penta (methylenephosphonic acid), 1-hydroxy-2-phenylethane-1, 1-diphosphonic acid, 2-hydroxyethane-1,1-diphosphonic acid, 1-hydroxyethane-1,1,2-triphosphonic acid, 2-hydroxyethane-1,1,2-triphosphonic acid, ethane-1,1-diphosphonic acid, and ethane-1,2-diphosphonic acid, amino tris(methylenephosphonic acid), or salts thereof.

Particularly useful are 1-hydroxyethyliciene-1,1-diphosphonic acid, aminotris(methylenephosphonic acid), diethylenetriamine-N,N,N',N'',N''-penta (methylenephosphonic acid), or salts thereof. The second compound is most useful.

One or more of the phosphonic or phosphinic acids defined above are present in conventional amounts, and generally in an amount of at least about 3 g/l.

It is particularly desirable that the reversal solution have a pH of from about 4 to about 8, and preferably at from about 5 to about 7. This can be achieved in suitable chemical acids or bases, or buffers, as needed.

Conventional color developing solutions can be used in the practice of this invention. In addition to an aromatic primary amino color developing agent, the color developing bath typically contains sequestering agents, buffering agents, preservatives, competing couplers and silver halide solvents.

Particularly useful aromatic primary amino color developing agents are the p-phenylenediamines and especially the N,N-dialkyl-p-phenylenediamines in which the alkyl groups or the aromatic nucleus can be substituted or unsubstituted. Examples of useful p-phenylenediamine color developing agents include but are not limited to: N,N-diethyl-p-phenylenediamine monohydrochloride, 4-N,N-diethyl-2-methylphenylene-diamine monohydrochloride, 4-(N-ethyl-N-2-methane-sulfonylaminoethyl)-2-methylphenylenediamine sesquisulfate monohydrate, 4-(N-ethyl-N-2-hydroxyethyl)-2-methyl-phenylenediamine sulfate, 4-N,N-diethyl-2,2'-methanesulfonylamino-ethyl-phenylenediamine hydrochloride, and others readily apparent to a skilled worker in the art.

Conventional pre-bleach or conditioning solutions can be used in the practice of the present invention, as described for example in the patents noted in the Background of the Invention. A preferred conditioning solution includes an aliphatic thiol bleach accelerating agent, a formaldehyde precursor (such as sodium formaldehyde bisulfite), sulfite ions as a preservative, and a metal ion sequestering agent. A secondary amine is an optional component.

The essential component of a bleaching bath useful in this invention is a bleaching agent that converts metallic silver to silver ions. Other common components of the bleaching bath include halides, sequestering agents and corrosion inhibitors. Ammonium or alkali metal salts of a ferric complex of an aminopolycarboxylic acid are particularly useful as bleaching agents but other metal complexes are known in the art, including binary and ternary complexes. Also of utility are the persulfate bleaching agents such as ammonium or alkali metal persulfates and peroxide bleaching agents. Bleaching agents can be used individually or in the form of mixtures of two or more bleaching agents.

A fixing solution converts all silver halide into soluble silver complexes that diffuse out of the emulsion layers. Fixing solution retained within the layers of the photographic element is removed in a subsequent water washing step. Thiosulfates, including ammonium thiosulfate and alkali metal thiosulfates (such as sodium thiosulfate and potassium thiosulfate), are particularly useful as fixing agents. Other components of the fixing solution include preservatives and sequestering agents.

A wide variety of different color reversal processes are well known in the art. For example, a single color developing step can be used when the coupling agents are incorporated in the photographic element or three separate color developing steps can be used in which coupling agents are included in the developing solutions. In order to provide shorter processing times, bleaching and fixing can be combined in a single step (known as a bleach-fixing step).

The photographic elements processed in the practice of this invention can be single or multilayer color elements. Multilayer color elements typically contain dye image-forming units sensitive to each of the three primary regions of the visible spectrum. Each unit can be comprised of a single emulsion layer or multiple emulsion layers sensitive to a given region of the spectrum. The layers of the element can be arranged in any of the various orders known in the art. In an alternative format, the emulsions sensitive to each of the three primary regions of the spectrum can be disposed as a single segmented layer. The elements can also contain other conventional layers such as filter layers, interlayers, subbing layers, overcoats and other layers readily apparent to one skilled in the art. A magnetic backing can be used as well as conventional supports.

Considerably more details of the element structure and components, and suitable methods of processing various types of elements are described in *Research Disclosure*, noted above. All types of emulsions can be used in the elements, including but not limited to, thin tabular grain emulsions, and either positive-working or negative-working emulsions.

The present invention is particularly useful for processing imagewise exposed and developed photographic elements containing arylpyrazolone type magenta dye forming color couplers. Such color couplers are well known in the art. One such compound is described in U.S. Pat. No. 5,037,725 (noted above).

The elements are typically exposed to suitable radiation to form a latent image and then processed as described above to form a visible positive color image.

The conditions (time and temperature) for the various steps of the method of this invention are well known in the art. The reversal step, in particular, is carried out for from about 45 to about 200 second at a temperature of from about 20° to about 40° C. Times and temperatures outside these ranges can be used if desired.

Processing according to the present invention can be carried out using conventional deep tanks holding processing solutions. Alternatively, it can be carried out using what is known in the art as "low volume thin tank" processing systems having either rack and tank or automatic tray designs. Such processing methods and equipment are described, for example, in U.S. Pat. No. 5,436,118 (Carli et al) and publications noted therein.

The following examples are provided for illustrative purposes only and are not intended to be limiting in any way. Unless otherwise indicated, all percentages are by weight.

EXAMPLES 1–7

Reversal Solutions With Various Biocides

Several reversal solutions of this invention were prepared as follows:

A concentrated reversal bath formulation (without biocide) was prepared with the following components:

Tap water 840.0 g/l

DEQUEST 2000* (50%) 125.36 g/l

Sodium hydroxide (50%) 78.0 g/l

Stannous chloride, anhydrous 33.0 g/l p-aminophenol 0.01 g/l

To provide 1 liter of solution.

* DEQUEST 2000 is a 50% (by weight) solution of aminotris(methylenephosphonic acid) available from Monsanto Co.

The concentrated solution was diluted to a working strength solution with tap water (19:1), and 90 ml aliquots were distributed into 120 ml sterile cups. The biocide being evaluated (at various concentrations) was added to a given cup along with 10 ml of an inoculum comprised of "seasoned" reversal bath solution from a commercial Hope 296 processing machine. The microbial concentration (various bacterial and fungal organisms) of the inoculum was at least about $10^6$ CFU/ml. Upon addition to the cups, the inoculum microbial concentration was thusly diluted 10:1 (to $10^5$ CFU/ml).

Each cup and solution was incubated at 30° C., and samples were taken from each cup after 1 and 4 days. The levels of CFU/ml was determined using the standard Millipore SPC Procedure, which includes:

1) Dispensing the sample into a SPC container.
2) Returning the SPC paddle to the container and placing the unit, grid side down, on the counter for 30 seconds.
3) Removing the SPC paddle and shaking off excess moisture, and pouring out the liquid in the container.
4) Replacing the SPC paddle and incubating the unit at 30° C. for 72 hours, allowing the bacteria to thrive on nutrient media that diffuses through the membrane grid, and
5) After incubation, removing the SPC paddle again and counting the bacteria colonies.

The following quaternary ammonium compounds were evaluated as the sole biocides in the samples noted above.

Example 1

Benzalkonium chloride (commercial mixture of alkyldimethylbenzyl ammonium chlorides).

Example 2

Cetylpyridinium chloride ("CPC").

Example 3

Cetyltrimethyl ammonium bromide ("CTAB").

Example 4

Cetyltrimethyl ammonium chloride ("CTAC").

Example 5

Cetyldimethylethyl ammonium bromide ("CDEAB").

Example 6

Commercial mixture of alkyltrimethyl ammonium bromides ("ATAB", available as "Cetrimide").

Example 7

Myristyltrimethyl ammonium bromide ("MTAB").

TABLE I below lists the results of microbial counts for some of the samples after 1 and four days incubation.

TABLE I

| SAMPLE | AMOUNT OF BIOCIDE (ppm) | 1 DAY CFU/ml | 4 DAYS CFU/ml |
|---|---|---|---|
| Control | 0 | >$10^5$ | >$10^5$ |
| Example 2 | 75 | <10 | <10 |
| Example 2 | 50 | 10 | 100 |
| Example 3 | 75 | <10 | <10 |
| Example 1 | 50 | 10 | <10 |
| Example 1 | 100 | <10 | <10 |

The results of these experiments showed that several quaternary ammonium compounds are useful as the sole biocides in reversal bath solutions.

Additional experiments were similarly carried out except that incubation of the samples was extended, and microbial counts were made after 1 and 7 days. TABLE II shows the results of these experiments.

TABLE II

| SAMPLE | AMOUNT OF BIOCIDE (ppm) | 1 DAY CFU/ml | 7 DAYS CFU/ml |
|---|---|---|---|
| Control | 0 | >$10^5$ | >$10^5$ |
| Example 4 | 50 | 10 | <10 |
| Example 5 | 50 | 100 | <10 |
| Example 6 | 50 | >$10^5$ | 100 |

These experiments demonstrated the usefulness of several quaternary ammonium compounds as the sole biocides in reversal bath solutions. "ATAB"(Example 6) was not useful at 50 ppm after 1 day, but it was effective after a longer period of time. Thus, some useful quaternary ammonium compounds may require routine optimization of concentration and incubation time in a reversal bath solution for maximum effectiveness.

Still additional experiments were similarly carried out with samples taken after 3 and 5 days incubation. TABLE III below shows the resulting data.

TABLE III

| SAMPLE | AMOUNT OF BIOCIDE (ppm) | 3 DAY CFU/ml | 5 DAYS CFU/ml |
|---|---|---|---|
| Control | 0 | >$10^5$ | >$10^5$ |
| Example 6 | 100 | <10 | <10 |
| Example 6 | 200 | <10 | <10 |

Further experiments were similarly carried out with additional samples taken after 3 and 7 days incubation. TABLE IV below shows the resulting data.

TABLE IV

| SAMPLE | AMOUNT OF BIOCIDE (ppm) | 3 DAY CFU/ml | 7 DAYS CFU/ml |
|---|---|---|---|
| Control | 0 | >$10^5$ | >$10^5$ |
| Example 6 | 100 | 100 | 100 |
| Fxample 7 | 100 | 100 | <10 |
| Example 7 | 200 | <10 | <10 |

As indicated by these data, the tested biocides are effective at various concentrations for after various usage time. Routine experimentation would readily enable a skilled artisan to determine the optimum concentration and usage time for a given quaternary ammonium compound for a given reversal bath solution and processing method (for example, with knowledge of the approximate level of microbial population).

Example 8

Processing Reversal Color Photographic Film With Preferred Reversal Solutions

"MTAB"(Example 7 above) was incorporated into a working strength reversal bath solution (noted above) as the sole biocide at 125 and 175 ppm. Each resulting reversal bath solution was used to process samples of conventional KODAK EKTACHROME ELITE 5045 reversal color photographic film in a processor similar to the commercially available Colex Model 7/6 EKTACHROME roller transport processor for a minimum of 3 tank turnovers. One tank turnover refers to the equivalent of replacing one tank volume with a combination of solution carried in from the previous processing tank and fresh replenisher solution. A fully seasoned processing solution requires about 3 tank turnovers.

The film processing utilized the following conventional reversal ("Process E–6") processing protocol at conventional temperatures:

| | |
|---|---|
| First Development* | 6 minutes |
| Water wash | 2 minutes |
| Reversal solution** | 2 minutes |
| Color development*** | 6 minutes |
| Conditioning**** | 2 minutes |
| Bleaching $ | 6 minutes |
| Fixing # | 4 minutes |
| Water wash | 4 minutes |
| Final wash ## | 1 minute |
| Drying | |

*First Development used conventional KODAK First Developer tor Process E-6.
**Reversal solution described above.
***Color development used conventional KODAK Color Developer, Process E-6.
****Conditioning using KODAK Prebleach & Replenisher, Process E-6.
$ Bleaching using conventional KODAK Bleach, Process E-6.
Fixing used conventional KODAK Fixer, Process E-6.
Final washing used KODAK Final Rinse, Process E-6.

After the noted period of processing time, samples of the reversal bath solution were taken and the microbial population was determined as described above using Millipore SPC samplers and procedure. TABLE V below lists the results obtained thereby.

TABLE V

| BIOCIDE | AMOUNT OF BIOCIDE (ppm) | 3 Tank Turnovers CFU/ml |
|---|---|---|
| "MTAB" | 125 | 10 |
| "MTAB" | 175 | <10 |

The invention has been described in detail with particular reference to preferred embodiments thereof, but it will be understood that variations and modifications can be effected within the spirit and scope of the invention.

We claim:

1. A photographic reversal solution comprising stannous ion present in an amount of from about 0.002 to about 0.02 mol/l, and a quaternary ammonium compound as the sole biocide, said quaternary ammonium compound having a molecular weight of from 175 to 440 and present in an amount of from about 50 to about 300 ppm.

2. The solution of claim 1 wherein said stannous ion concentration is from about 0.004 to about 0.01 mol/l.

3. The solution of claim 1 wherein said quaternary ammonium compound has a molecular weight of from about 250 to about 420.

4. The solution of claim 1 wherein said quaternary ammonium compound is represented by the structure III:

$$R_5(R_6)N^+(R_7)R_8 \ X^-$$

wherein $R_5$, $R_6$, $R_7$ and $R_8$ are independently nonpolymeric aliphatic, heterocyclic or carbocyclic radicals and $X^-$ is a monovalent cation.

5. The solution of claim 4 wherein said quaternary amine compound is nonyltrimethyl ammonium bromide, dodecyltrimethyl ammonium chloride, hexadecyltrimethyl ammonium bromide, hexadecyltrimethyl ammonium chloride, benzyltriethyl ammonium chloride, didodecyldimethyl ammonium bromide, benzyldimethylphenyl ammonium chloride, tetrahexyl ammonium chloride, stearyldimethylbenzyl ammonium chloride, cetylpyridinium chloride, benzalkonium chloride, a mixture of alkyltrimethyl ammonium bromides, myristyltrimethyl ammonium bromide, or mixtures thereof.

6. The solution of claim 1 wherein said quaternary ammonium compound is myristyltrimethyl ammonium bromide.

7. The solution of claim 1 further comprising a stannous ion stabilizer, an organic phosphonic acid or phosphinic acid chelating agent, a chemical base, a buffer, or a mixture thereof.

8. The solution of claim 1 having a ph of from about 4 to about 8.

9. The solution of claim 1 further comprising an organic phosphonic or phosphinic acid chelating agent at a concentration of at least about 3 g/l.

10. The solution of claim 9 wherein said organic phosphonic or phosphinic acid chelating agent is represented by the structure I or II:

$$R_1N \ (CH_2PO_nM_2)_2 \quad (I)$$

$$R_2R_3C \ (PO_nM_2)_2 \quad (II)$$

wherein n is 2 or 3, $R_1$ is hydrogen, alkyl of 1 to 12 carbon atoms, alkylaminoalkyl wherein each alkyl portion has 1 to 12 carbon atoms, alkoxyalkyl of 2 to 12 carbon atoms, cycloalkyl of 5 to 10 carbon atoms in the ring, or a 5- to 10-membered heterocyclic group having one or more nitrogen, oxygen or sulfur atoms in the heterocyclic ring, $R_2$ is hydrogen, alkyl of 1 to 12 carbon atoms, aryl of 6 to 10 carbon atoms in the aromatic ring, cycloalkyl of 5 to 10 carbon atoms in the ring, a 5- to 10-membered heterocyclic group having one or more nitrogen, oxygen or sulfur atoms in the heterocyclic ring, $-PO_nM_2$ or $-CHR_4PO_nM_2$, $R_3$ and $R_4$ are independently hydrogen, hydroxy, alkyl of 1 to 12 carbon atoms, or $-PO_nM_2$, and M is hydrogen or a water-soluble cation.

11. A photographic reversal solution having a pH of from about 4 to about 7 and comprising:

a) stannous ion at a concentration of from about 0.004 to about 0.01 mol/l, b) a quaternary ammonium compound as the sole biocide at a concentration of from about 50 to about 250 ppm, said quaternary ammonium compound being myristyltrimethyl ammonium bromide, c) a stannous ion stabilizer, and d) an organic phosphonic or phosphinic acid chelating agent.

12. A method of processing a color reversal photographic film comprising:

A) contacting an imagewise exposed color reversal photographic film with a reversal solution comprising stannous ion present in an amount of from about 0.002 to about 0.02 mol/l and a quaternary ammonium compound as the sole biocide, said quaternary ammonium compound having a molecular weight of from 175 to 440 and present in an amount of from about 50 to about 300 ppm, and B) color developing said film.

13. The method of claim 12 further comprising bleaching, fixing, and washing or stabilizing said color developed film.

14. The method of claim 12 wherein said quaternary ammonium compound is represented by the structure III:

$$R_5(R_6)N^+(R_7)R_8 \ X^-$$

wherein $R_5$, $R_6$, $R_7$ and $R_8$ are independently nonpolymeric aliphatic, heterocyclic or carbocyclic radicals, and $X^-$ is a monovalent cation.

15. The method of claim 12 wherein said quaternary ammonium compound is nonyltrimethyl ammonium bromide, dodecyltrimethyl ammonium chloride, hexadecyltrimethyl ammonium bromide, hexadecyltrimethyl ammonium chloride, benzyltriethyl ammonium chloride, didodecyldimethyl ammonium bromide, benzyldimethylphenyl ammonium chloride, tetrahexyl ammonium chloride, stearyldimethylbenzyl ammonium chloride, cetylpyridinium chloride, benzalkonium chloride, a mixture of alkyltrimethyl ammonium bromides, myristyltrimethyl ammonium bromide, or mixtures thereof.

16. The method of claim 12 wherein said reversal solution comprising stannous ion at a concentration of from about 0.004 to about 0.01 mol/l, said quaternary ammonium compound is present at a concentration of from about 50 to about 250 ppm, and said solution further comprises an organic phosphonic or phosphinic acid chelating agent at a concentration of at least about 3 g/l.

17. The method of claim 16 wherein said quaternary ammonium compound is myristyltrimethyl ammonium bromide.

\* \* \* \* \*